(12) United States Patent
Senzig

(10) Patent No.: US 6,304,625 B1
(45) Date of Patent: Oct. 16, 2001

(54) DOSE INSTRUMENTATION METHODS AND APPARATUS FOR COLLIMATED CT IMAGING SYSTEMS

(75) Inventor: Robert P. Senzig, Germantown, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/452,684

(22) Filed: Dec. 1, 1999

(51) Int. Cl.$^7$ .............................. A61B 6/00; G01N 23/00; G21K 1/12; H05G 1/60
(52) U.S. Cl. .................... 378/4; 378/16; 378/21; 378/97; 378/108
(58) Field of Search ................................ 378/4, 16, 64, 378/65, 97, 108, 21, 62

(56) References Cited

U.S. PATENT DOCUMENTS 5,761,257 6/1998 Toth et al. .

Primary Examiner—Robert H. Kim
Assistant Examiner—Courtney Thomas
(74) Attorney, Agent, or Firm—Armstrong Teasdale, LLP; Christian G. Cabou

(57) ABSTRACT

One embodiment of the present invention is a method for measuring a radiation dose of a patient applied by a computerized tomography (CT) imaging system having a radiation source emitting a radiation beam and a radiation detector. The method includes steps of: scanning a patient with the radiation beam; imaging the patient utilizing radiation detected by the radiation detector; and estimating a patient radiation dose from said imaging utilizing a measurement of radiation delivered to only a portion of the detector during said imaging.

The present invention permits the advantages of a post-patient collimated detector array to be realized while providing an accurate estimate of patient radiation dosage.

26 Claims, 4 Drawing Sheets

DOSE INSTRUMENTATION METHODS AND APPARATUS FOR COLLIMATED CT IMAGING SYSTEMS

BACKGROUND OF THE INVENTION

This invention relates generally to computed tomography (CT) imaging systems, and more particularly to methods and apparatus for measuring radiation dosages in post-patient collimated CT imaging systems.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

At least one known CT imaging system employs post-patient collimation, one purpose of which is to reduce slice broadening. For example, a mechanical collimator is interposed between the patient and a radiation detector matrix. The mechanical collimator is comprised of a strip of material essentially opaque to x-rays, such as lead. The strip covers a detector assembly housing a detector array, and has a slot aligned along the detector elements to collimate x-rays impinging on the detector elements.

In imaging systems without post-patient collimation, an x-ray dose delivered to a patient can be directly measured from a measurement of the x-rays reaching the detector. However, in systems employing post-patient collimation, not all of the x-ray beam actually reaches the detector during dose testing, because some of it is blocked by the post-patient collimator. As a result, patient dosage cannot be accurately determined, because an unknown percentage of the radiation dose received by a patient never reaches the detection matrix.

It would therefore be desirable if methods and apparatus were available to provide accurate dose measurement even when post-patient collimation is employed.

BRIEF SUMMARY OF THE INVENTION

There is therefore provided, in one embodiment of the present invention, a method for measuring a radiation dose of a patient applied by a computerized tomography (CT) imaging system having a radiation source emitting a radiation beam and a radiation detector. The method includes steps of: scanning a patient with the radiation beam; imaging the patient utilizing radiation detected by the radiation detector; and estimating a patient radiation dose from said imaging utilizing a measurement of radiation delivered to only a portion of the detector during said imaging.

Utilizing methods and apparatus of the present invention, the advantages of a post-patient collimated detector array can be realized. At the same time, an accurate estimate of patient radiation dosage can be determined.

DETAILED DESCRIPTION OF THE INVENTION

Figure 1:
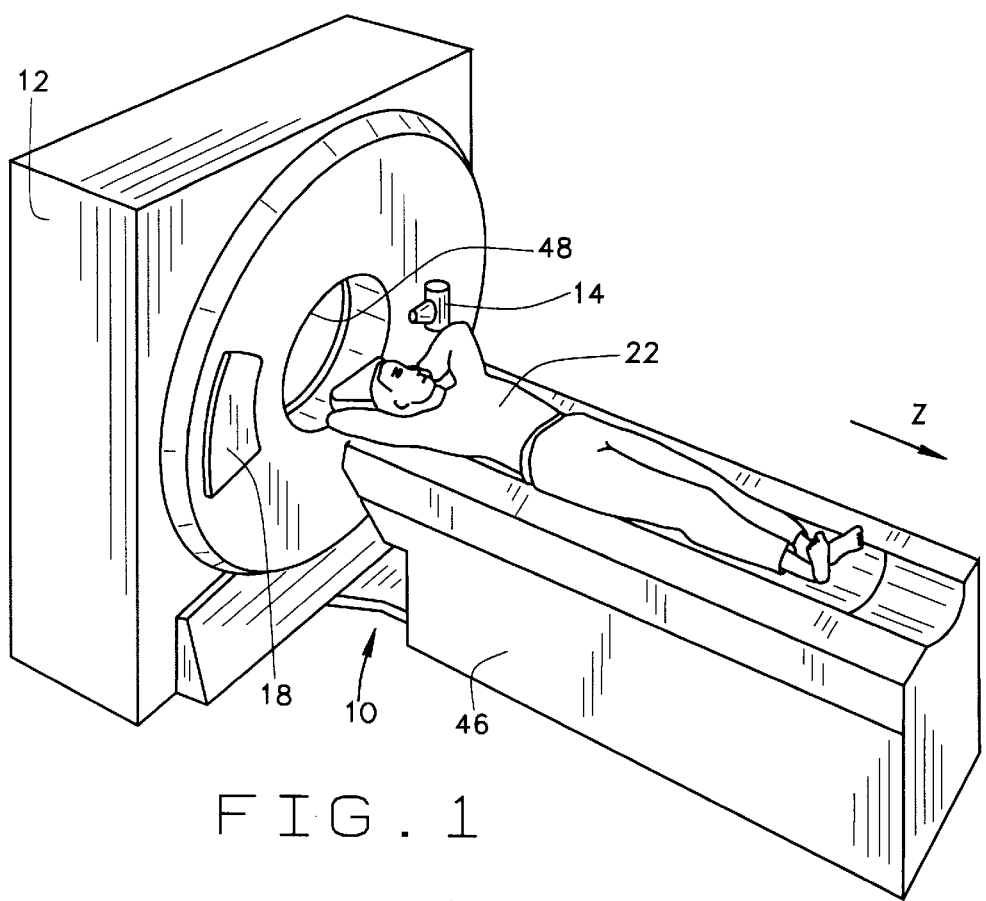
FIG. 1 is a pictorial view of a CT imaging system.
Figure 2:
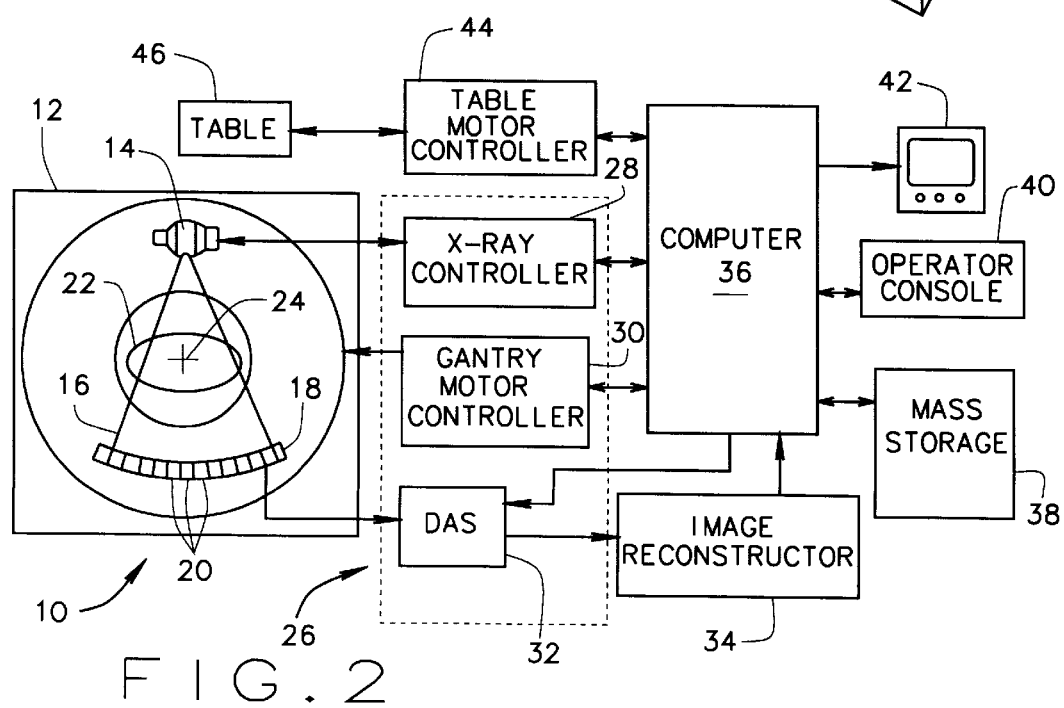
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed, in part, by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. The rotation of gantry 12 also defines a z-axis perpendicular to a plane of gantry 12. Linear dimensions parallel to the z-axis are denoted herein as "thicknesses."

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
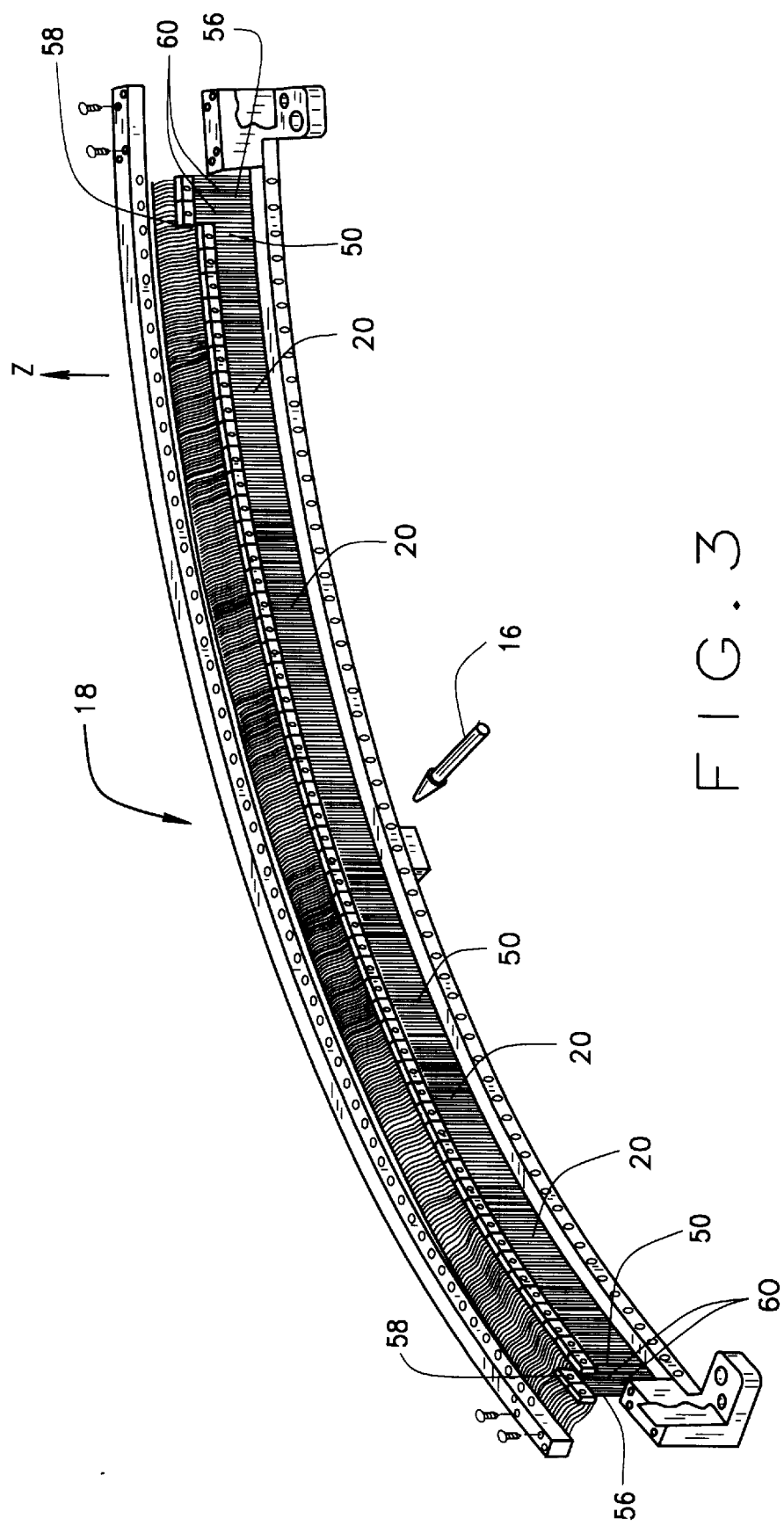
FIG. 3 is a perspective view of a CT system detector array.
Figure 4:
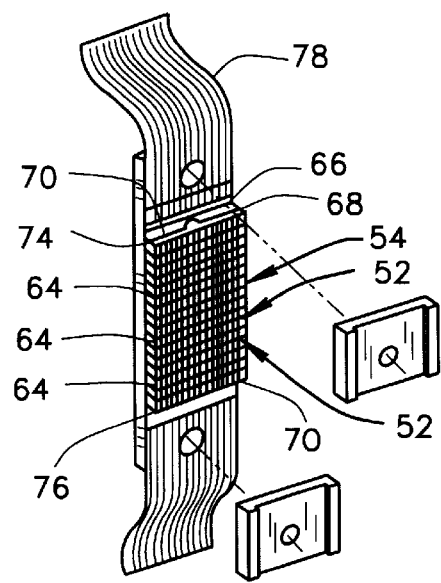
FIG. 4 is a perspective view of a detector module shown in FIG. 3.

As shown in FIGS. 3 and 4, detector array 18 includes a plurality of detector or imaging modules 20 that together form a imaging portion or region 50 of detector array 18. In one embodiment, each detector module 20 includes a high-density semiconductor array 52 and a multidimensional scintillator array 54 positioned above and adjacent to semiconductor array 52. Detector array 18 also has at least one additional measuring module 56 positioned adjacent at least one end 58 of detector array 18. As used herein, "adjacent a longitudinal end" means touching an end 58, or slightly separated therefrom but sufficiently close thereto so as to intercept a portion of x-ray beam 16. For example, detector array 18 comprises measuring modules 56 touching both opposite longitudinal ends 58 of detector array 18. Measuring modules 56 form measuring portions or regions 60 of detector array 18. Measuring regions 60 are somewhat thicker in z-axis extent than imaging portion 50. In one embodiment, this difference in thickness is a produced by using different size detector modules 20 for measuring region 60 and imaging portion 50 of detector array 18. A post-patient collimator (not shown in FIGS. 3 or 4) is used to provide beam collimation of x-ray beam 16 to a thickness less than or equal to that of imaging portion 50, while allowing a full measuring region 60 thickness of x-ray beam 16 to strike measuring region 60.

Figure 5:
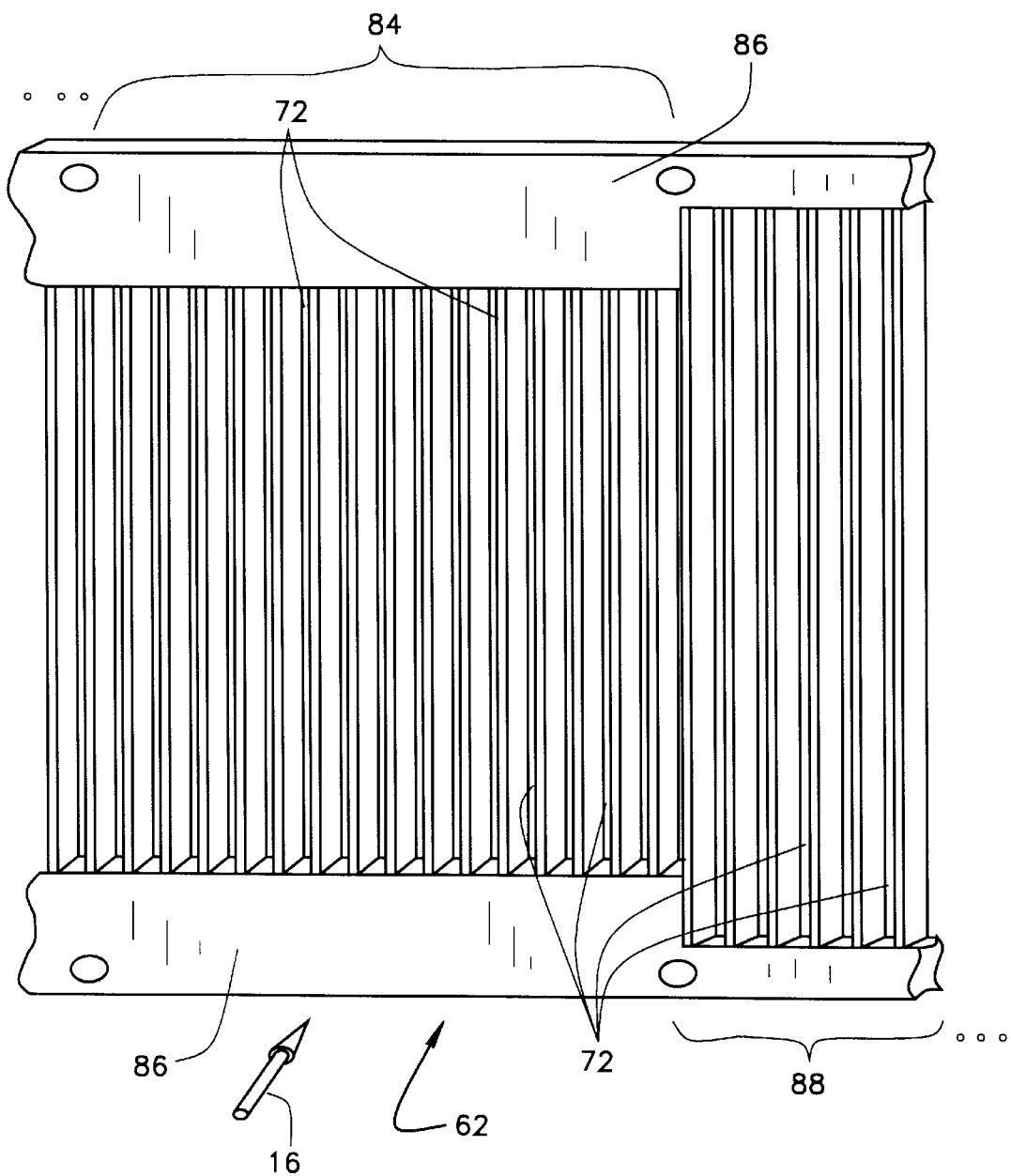
FIG. 5 is a perspective view of a portion of a post-patient collimator used in conjunction with the CT system detector array of FIG. 3.

In one embodiment, imaging portion 50 and measuring region 60 are the same thickness, and a post-patient collimator 62 (a portion of which is shown in FIG. 5) providing both scatter collimation and beam thickness collimation is positioned above and adjacent imaging portion 50 of scintillator array 54. One portion 84 of post-patient collimator 62 provides both types of collimation for imaging portion 50 of scintillator array 54. Collimator 62 provides scatter collimation with slots 72, and beam collimation with rails 86, which are thicker over imaging portion 50 of scintillator array 54 than over measuring portions 60. Due to the opaqueness of the rails 86 blocking out a portion of x-ray beam 16 over detector array 18, post-patient collimator 62 provides beam collimation of x-ray beams 16 before such beams impinge upon scintillator array 54. A portion 88 of post-patient collimator 62 has thinner rails 86 and therefore does not provide beam collimation.

In one embodiment, x-ray beam 16 is subjected to post-patient beam collimation so that less than a thickness of beam 16 contributing to a radiation dose to patient 22 impinges imaging portion 50 of scintillator array 54. As a result, a measurement of radiation dose cannot be made solely from radiation striking imaging portion 50. However, the post-patient beam collimation is not applied in a manner that affects a peripheral portion of x-ray beam 16. Therefore, a full thickness of x-ray 10 beam 16 impinges measuring portions 60 of scintillator array 54 and this full thickness is used to estimate the radiation dose of patient 22 during imaging.

"A full thickness of x-ray beam 16," as used herein refers to a thickness encompassing essentially all of the radiation energy of x-ray beam 16 in a direction parallel to the z-axis. Because post-patient collimation of x-ray beam 16 blocks a portion of the energy of x-ray beam 16, a measurement of a full thickness of x-ray beam 16 is more representative of a total patient 22 than would be a measurement of the post-patient beam collimated portion. In one embodiment, more accurate estimations of patient 22 radiation dosage are provided by configuring imaging system 10 being configured so that non-post patient collimated portions of x-ray beam 16 are neither attenuated by patient 22 nor significantly attenuated by portions of imaging system 10 before striking measuring portions 60.

Semiconductor array 52 includes a plurality of photodiodes 64, a switch apparatus 66, and a decoder 68. Photodiodes 64 are, for example, individual photodiodes. A multidimensional diode array construction is also acceptable. Photodiodes 64 are deposited or formed on a substrate (not shown). Scintillator array 54, as known in the art, is positioned over and adjacent photodiodes 64. Photodiodes 64 are optically coupled to scintillator array 54 and have electrical output lines 70 for transmitting signals representative of the light output by scintillator array 54. Each photodiode 64 produces a separate low level analog output signal that is a measurement of beam attenuation for a specific scintillator of scintillator array 54. Photodiode output lines 70 are, for example, physically located on one side of module 20 or on a plurality of sides of module 20. In the embodiment illustrated in FIG. 4, photodiode outputs 70 are located at opposing sides of the photodiode array.

In one embodiment and as shown in FIG. 3, detector array 18 includes fifty-seven detector or imaging modules 20. Each detector module 20 includes a semiconductor array 52 and scintillator array 54, each having an array size of 16×16. As a result, array 18 comprises sufficient detector modules 20 for 16 rows and 912 columns of imaging (16×57 modules), thus allowing up to N=16 simultaneous slices of data to be collected along a z-axis with each rotation of gantry 12. In another embodiment, detector modules 20 are single-slice detector modules having an array size of 1 row by 16 columns, so that array 18 has sufficient detector modules 20 for 1 row and 912 columns. However, the invention is not limited to a specific number of rows or slice thickness, or to a specific array size or number of columns. Slots 72 of post-patient collimator 62 are aligned over each column of detector modules 20 to collimate x-rays of x-ray beam 16 that impinge thereon.

Measuring module 56 is sufficiently thick to detect an entire thickness of x-ray beam 16 as measured in a direction along the z-axis. In other words, an effective thickness of measuring module 56, in one embodiment, is as thick or thicker than a thickness of all slices measurable by measuring portion 50 and as thick as that portion of x-ray beam 16 having sufficient intensity to contribute to a patient radiation dose. In one embodiment, detection elements of measuring module 56 are scintillators and photodiodes similar to those of imaging modules 20. However, measuring module 56 need not be configured for multiple slice operation nor have the same size or number of detection elements as imaging module 58. In one embodiment, measuring module 56 is segmented similarly to imaging module 20, allowing all or portions of its measuring region to be used for dose measurement when impinged by a partially obstructed x-ray beam.

In one multi-slice detector array embodiment, switch apparatus 66 is a multidimensional semiconductor switch array of similar size as that portion of semiconductor array 52 that includes detector or imaging modules 20. Switch apparatus 66 is coupled between semiconductor array 52 and DAS 32. Semiconductor device 66, in one embodiment, includes two semiconductor switches 74 and 76. Switches 74 and 76 each include a plurality of field effect transistors (FETs) (not shown) arranged as a multidimensional array. Each FET includes an input line electrically connected to one of the respective photodiode output lines 70, an output line, and a control line (not shown). FET output and control lines are electrically connected to DAS 32 via a flexible electrical cable 78. Particularly, about one-half of photodiode output lines 70 are electrically connected to each FET input line of switch 74 with the other one-half of photodiode output lines 70 electrically connected to FET input lines of switch 76. Decoder 68 controls the operation of switch apparatus 66 to enable, disable, or combine photodiode outputs in accordance with a desired number of slices and slice resolutions for each slice.

Decoder 68 is a decoder chip or an FET controller as known in the art. Decoder 68 includes a plurality of output and control lines coupled to switch apparatus 66 and DAS 32. Particularly, the decoder outputs are electrically coupled to the switch apparatus control lines to enable switch apparatus 66 to transmit the proper data from the switch apparatus inputs to the switch apparatus outputs. Utilizing decoder 68, specific FETs within switch apparatus 66 are enabled, disabled, or combined so that specific photodiode outputs are electrically connected to CT system DAS 32 to provide selected slice thicknesses and/or a selected number of image slices.

Outputs of measuring modules 56 are also electrically connected to CT system DAS 32, but data obtained from these outputs are not processed as image data. Instead, in one embodiment, DAS 32 and image reconstructor 34 recognize these inputs as providing x-ray dose data and pass this data on to computer 36, which calculates an x-ray dosage based upon data received from measuring modules 56.

In one embodiment, imaging system 10 scans patient 22 with radiation beam 16 and images patient 22 utilizing radiation detected by detector array 18.

Patient radiation dosage is estimated from a measurement of radiation delivered to only a portion 60 of detector array 18 during imaging.

Figure 6:
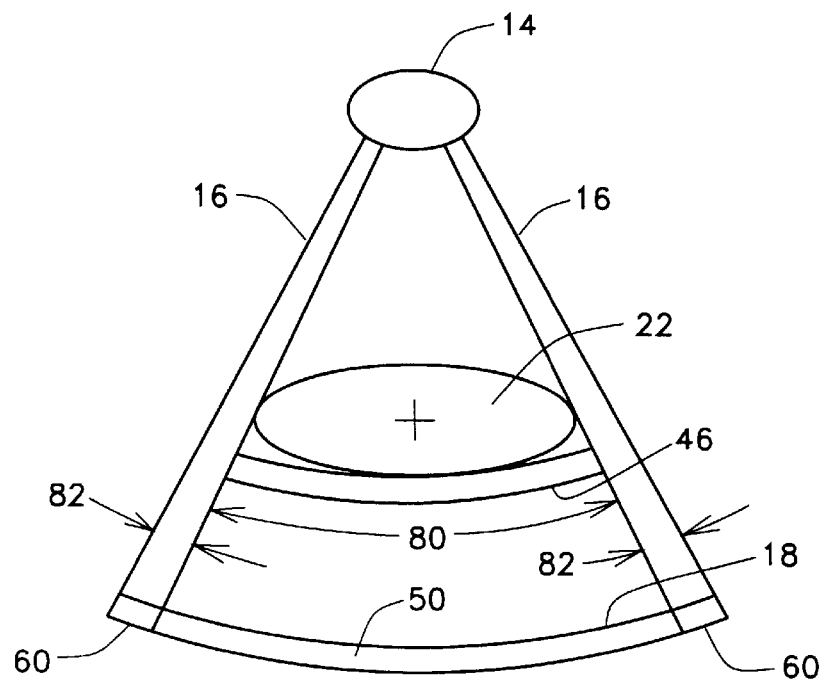
FIG. 6 is a simplified cross-sectional view of an x-ray beam directed at the detector array of FIG. 3 as used in the CT imaging system of FIG. 1.

In one embodiment and referring to FIG. 6, x-ray source 14 is configured to project an x-ray beam 16 towards detector array 18, which includes a beam collimated, imaging portion 50 and measuring portions 60 that are not beam collimated. X-ray source 14 and detector array 18 are mounted on a rotating gantry 12, which is not shown in the simplified view of FIG. 6. Table or patient support 46 supports patient 22 between x-ray source 14 and detector array 18 so that at least a portion 80 of x-ray beam 16 passes through patient 22 and is thereby attenuated. The attenuated radiation beam 80 is beam collimated to reduce its thickness and impinges on imaging portion 50. Data representative of images of patient 22 are collected therefrom.

Another portion 82 of x-ray beam 16 is essentially unobstructed by patient 22 and impinges without beam collimation on measuring portions 60. Data from one or both measuring portions 60 is used by imaging system 10 to compute a patient x-ray dose. In one embodiment, x-ray fan beam 16 has a thickness in a z-axis direction no greater than that of measuring portions or regions 60 to provide a measurement representative of the entire x-ray dose patient 22 receives. However, x-ray beam 16 has a greater thickness than collimated portion 80 to provide a full selection of image slices and thicknesses. Portion 82 of x-ray beam 16 is of greater thickness than post-patient beam collimated portion 80 impinging on imaging portion. Computer 36 receives measurements from measuring portion (or portions) 60 and utilizes these measurements to compute a radiation dose. In one embodiment, this computation is based on an assumption that dosage across the fan beam 16 thickness is uniform. A full thickness of portion 82 of beam 16 is used for the estimation.

Patient 22 is thus imaged utilizing radiation beam 16 and a post-patient collimated detector, i.e., imaging portion 50 of detector array 18. Dose measurements are made utilizing a full thickness of unobstructed (i.e., non-beam collimated) portion 82 of radiation beam 16 and a detector having portions that are not beam collimated, i.e., measuring portions 60 of detector array 18.

In one embodiment, there is no post-patient collimation, but detector array 18 has an imaging portion 50 that is not as thick as measuring portion or portions 60. A thickness of radiation beam 16 that is as thick or thicker than imaging portion 50 of detector array 18 is measured by measuring portion or portions 60 to estimate patient radiation dose.

Although the invention has been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Also, the present invention may be used with systems performing either axial or helical scans, or both types of scans. Accordingly, the spirit and scope of the invention are to be limited only by the terms of the appended claims.

What is claimed is:

1. A method for measuring a radiation dose of a patient applied by a computerized tomography (CT) imaging system having a radiation source emitting a radiation beam and a radiation detector, said method comprising the steps of:

scanning a patient with the radiation beam;

imaging the patient utilizing radiation detected by the radiation detector; and estimating a patient radiation dose from said imaging utilizing a measurement of radiation delivered to only a portion of the detector during said imaging.

2. A method in accordance with claim 1, wherein imaging a patient utilizing radiation detected by the radiation detector comprises the step of imaging the patient utilizing radiation detected from a first portion of the radiation beam; and estimating a patient radiation dose from said imaging comprises the step of estimating a total patient radiation dose utilizing radiation detected from a second portion of the radiation beam, wherein a thickness of the radiation utilized for estimating the patient radiation dose is greater than a thickness of the radiation utilized to image the patient.

3. A method in accordance with claim 2 further comprising the step of post-patient beam collimating the first portion of the radiation beam to reduce a thickness of the first portion of the radiation beam relative to the second portion of the radiation beam.

4. A method in accordance with claim 3 wherein estimating a patient radiation dose utilizing radiation detected from the second portion of the radiation beam comprises the step of estimating a patient radiation dose utilizing a full thickness of the second portion of the radiation beam.

5. A method in accordance with claim 4 wherein estimating a patient radiation dose utilizing a full thickness of the second portion of the radiation beam comprises the step of estimating a patient radiation dose utilizing a full thickness of the second portion of the radiation beam essentially unattenuated by the patient.

6. A method in accordance with claim 3 wherein post-patient beam collimating the first portion of the radiation beam comprises the step of post-patient beam collimating the first portion of the radiation beam to reduce a thickness of the first portion of the radiation beam relative to both the second portion of the radiation beam and a third portion of the radiation beam, the first portion of the radiation beam being between the second and the third portions; and estimating a patient radiation dose utilizing radiation detected from a second portion of the radiation beam comprises the step of estimating a patient radiation dose utilizing radiation detected from both the second and the third portion of the radiation beam, wherein a thickness of radiation from both the second and the third portion of the radiation beam utilized for estimating the patient radiation dose is greater than a thickness of radiation utilized to image the patient.

7. A method in accordance with claim 6 wherein estimating a patient radiation dose utilizing radiation detected from both the second and the third portions of the radiation beam comprises the step of estimating patient radiation dose utilizing a full thickness of the second and third portions of the radiation beam.

8. A method in accordance with claim 7 wherein estimating patient radiation dose utilizing a full thickness of the second and third portions of the radiation beam comprises the step of estimating patient radiation dose utilizing a full thickness of the second and third portions of the radiation beam essentially unattenuated by the patient.

9. A method in accordance with claim 2 wherein measuring a patient radiation dose utilizing radiation detected from the second portion of the radiation beam comprises the step of measuring a portion of the radiation beam striking the detector that is essentially unattenuated by the patient.

10. A method in accordance with claim 2 wherein the detector has an imaging portion having a first thickness and a measuring portion having a second thickness greater than the first thickness, and imaging the patient utilizing radiation detected from a first portion of the radiation beam comprises the step of imaging the patient utilizing no more than a first thickness of the radiation beam; and estimating a patient radiation dose utilizing radiation detected from a second portion of the radiation beam comprises the step of estimating a patient radiation dose utilizing the measuring portion of the detector and a thickness of the radiation beam greater than the first thickness.

11. A method in accordance with claim 10 wherein imaging the patient utilizing no more than a first thickness of the radiation beam comprises imaging the patient utilizing the imaging portion of the detector.

12. A method in accordance with claim 11 wherein estimating a patient radiation dose utilizing the measuring portion of the detector and a thickness of the radiation beam greater than the first thickness comprises measuring a full thickness of the radiation beam utilizing the measuring portion of the detector.

13. A method in accordance with claim 10 wherein the detector comprises two measuring portions at opposite ends of the imaging portion, and estimating a patient radiation dose comprises estimating a patient radiation dose utilizing radiation detected from both a second and a third portion of the radiation beam utilizing the two measuring portions of the detector.

14. A computerized tomography (CT) imaging system having a radiation source emitting a radiation beam and a radiation detector, said CT imaging system being configured to:

scan a patient with said radiation beam;

image the patient utilizing radiation detected by said radiation detector; and estimate a patient radiation dose from said imaging utilizing a measurement of radiation delivered to only a portion of said detector during said imaging.

15. An imaging system in accordance with claim 14, wherein said system being configured to image a patient utilizing radiation detected by said radiation detector comprises said system being configured to image the patient utilizing radiation detected from a first portion of said radiation beam; and said system being configured to estimate a patient radiation dose from said imaging comprises said system being configured to estimate a total patient radiation dose utilizing radiation detected from a second portion of said radiation beam, wherein a thickness of said radiation utilized for estimating said patient radiation dose is greater than a thickness of said radiation utilized to image the patient.

16. An imaging system in accordance with claim 15 further configured to post-patient beam collimate said first portion of said radiation beam to reduce a thickness of said first portion of said radiation beam relative to said second portion of said radiation beam.

17. An imaging system in accordance with claim 16 wherein said system being configured to estimate a patient radiation dose utilizing radiation detected from said second portion of said radiation beam comprises said system being configured to estimate a patient radiation dose utilizing a full thickness of said second portion of said radiation beam.

18. An imaging system in accordance with claim 17 wherein said system being configured to estimate a patient radiation dose utilizing a full thickness of said second portion of said radiation beam comprises said system being configured to estimate a patient radiation dose utilizing a full thickness of said second portion of said radiation beam essentially unattenuated by the patient.

19. An imaging system in accordance with claim 16 wherein said system being configured to post-patient beam collimate said first portion of said radiation beam comprises said system being configured to post-patient beam collimate said first portion of said radiation beam to reduce a thickness of said first portion of said radiation beam relative to both said second portion of said radiation beam and a third portion of said radiation beam, said first portion of said radiation beam being between said second and said third portions; and said system being configured to estimate a patient radiation dose utilizing radiation detected from a second portion of said radiation beam comprises said system being configured to estimate a patient radiation dose utilizing radiation detected from both said second and said third portions of said radiation beam, wherein a thickness of radiation from both said second and said third portions of said radiation beam utilized for estimating the patient radiation dose is greater than a thickness of radiation utilized to image the patient.

20. An imaging system in accordance with claim 19 wherein said system being configured to estimate a patient radiation dose utilizing radiation detected from both said second and said third portions of said radiation beam comprises said system being configured to estimate patient radiation dose utilizing a full thickness of said second and said third portions of said radiation beam.

21. An imaging system in accordance with claim 20 wherein said system being configured to estimate patient radiation dose utilizing a full thickness of said second and said third portions of said radiation beam comprises said system being configured to estimate patient radiation dose utilizing a full thickness of said second and said third portions of said radiation beam essentially unattenuated by the patient.

22. An imaging system in accordance with claim 15 wherein said system being configured to measure a patient radiation dose utilizing radiation detected from said second portion of said radiation beam comprises said system being configured to measure a portion of said radiation beam striking said detector that is essentially unattenuated by the patient.

23. An imaging system in accordance with claim 15 wherein said detector comprises an imaging portion having a first thickness and a measuring portion having a second thickness greater than said first thickness, and said system being configured to image the patient utilizing radiation detected from a first portion of said radiation beam comprises said system being configured to image the patient utilizing no more than a first thickness of said radiation beam; and said system being configured to estimate a patient radiation dose utilizing radiation detected from a second portion of said radiation beam comprises said system being configured to estimate a patient radiation dose utilizing said measuring portion of said detector and a thickness of said radiation beam greater than said first thickness.

24. An imaging system in accordance with claim 23 wherein said system being configured to image the patient utilizing no more than a first thickness of said radiation beam comprises imaging the patient utilizing said imaging portion of said detector.

25. An imaging system in accordance with claim 24 wherein said system being configured to estimate a patient radiation dose utilizing said measuring portion of said detector and a thickness of said radiation beam greater than said first thickness comprises said system being configured to measure a full thickness of said radiation beam utilizing said measuring portion of said detector.

26. An imaging system in accordance with claim 23 wherein said detector comprises two measuring portions at opposite ends of said imaging portion, and said system being configured to estimate a patient radiation dose comprises said system being configured to estimate a patient radiation dose utilizing radiation detected from both a second and a third portion of said radiation beam utilizing said two measuring portions of said detector.

* * * * *

UNITED STATES PATENT AND TRADEMARK OFFICE
CERTIFICATE OF CORRECTION

PATENT NO. : 6,304,625 B1
DATED : October 16, 2001
INVENTOR(S) : Robert P. Senzig It is certified that error appears in the above-identified patent and that said Letters Patent is hereby corrected as shown below:

Column 3,
Line 25, delete "a".
Line 58, delete "10".

Column 5,
Line 36, merge paragraph starting with "Patient radiation dosage ..." with the preceding paragraph starting with "In one embodiment, imaging system 10 scans patient 22 ...".

Signed and Sealed this

Fifteenth Day of April, 2003

JAMES E. ROGAN
*Director of the United States Patent and Trademark Office*